United States Patent [19]

Böger et al.

[11] Patent Number: 4,812,468
[45] Date of Patent: * Mar. 14, 1989

[54] PHENYLCARBOXIMIDATES AS PESTICIDES

[75] Inventors: Manfred Böger, Weil am Rhein, Fed. Rep. of Germany; Jozef Drabek, Oberwil, Switzerland

[73] Assignee: Ciba-Geigy Corporation, Ardsley, N.Y.

[*] Notice: The portion of the term of this patent subsequent to Feb. 2, 2005 has been disclaimed.

[21] Appl. No.: 120,288

[22] Filed: Nov. 13, 1987

Related U.S. Application Data

[63] Continuation of Ser. No. 658,004, Oct. 4, 1984, Pat. No. 4,723,015.

[30] Foreign Application Priority Data

Oct. 17, 1983 [CH]  Switzerland ............... 5627/83
Aug. 13, 1984 [CH]  Switzerland ............... 3870/84

[51] Int. Cl.$^4$ .................. C07D 213/63; A01N 43/40
[52] U.S. Cl. ........................ 514/346; 546/291
[58] Field of Search ..................... 546/291; 514/346

[56] References Cited

U.S. PATENT DOCUMENTS 4,711,900 12/1987 Varma et al. ................... 546/291

Primary Examiner—Mary C. Lee
Assistant Examiner—Robert C. Whittenbaugh
Attorney, Agent, or Firm—Kevin T. Mansfield; Edward Mc C. Roberts

[57] ABSTRACT

The invention relates to novel substituted N-[[[pyridyloxyphenyl]amino]carbonyl]phenylcarboximidates of the formula

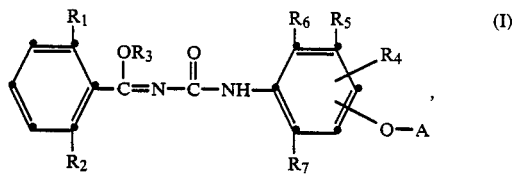

wherein
$R_1$ is hydrogen, halogen, methyl or methoxy,
$R_2$ is halogen, methyl, trifluoromethyl or methoxy,
$R_3$ is $C_1$-$C_5$alkyl, $C_1$-$C_3$haloalkyl containing 1 to 3 halogen atoms, allyl or propargyl,
$R_4$ and $R_5$ are each independently of the other hydrogen, halogen, methyl or trifluoromethyl,
$R_6$ and $R_7$ are hydrogen, and
A is the

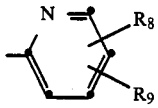

radical, in which $R_8$ is hydrogen, chlorine, trifluoromethyl or perhalogenated ethyl, and $R_9$ is hydrogen, halogen, methoxy or ethoxy;

to the preparation of these novel compounds and to compositions containing them for controlling insects and representatives of the order Acarina. The novel compounds are especially effective against plant-destructive insects.

15 Claims, No Drawings

PHENYLCARBOXIMIDATES AS PESTICIDES

This is a continuation of application Ser. No. 658,004 filed on Oct. 4, 1984 now U.S. Pat. No. 4,723,015.

The present invention relates to novel substituted N-[[[pyridyloxyphenyl]amino]carbonyl]phenylcarboximides, to the preparation thereof, and to the use thereof in pest control.

Specifically, the invention relates to compounds of the formula I

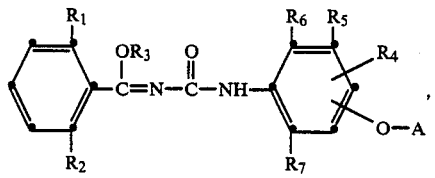

wherein
$R_1$ is hydrogen, halogen, methyl or methoxy,
$R_2$ is halogen, methyl, trifluoromethyl or methoxy,
$R_3$ is $C_1$-$C_5$alkyl, $C_1$-$C_3$haloalkyl containing 1 to 3 halogen atoms, allyl or propargyl,
$R_4$ and $R_5$ are each independently of the other hydrogen, halogen, methyl or trifluoromethyl,
$R_6$ and $R_7$ are hydrogen, and
A is the

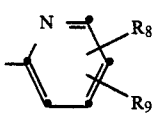

radical, in which $R_8$ is hydrogen, chlorine, trifluoromethyl or perhalogenated ethyl, and $R_9$ is hydrogen, halogen, methoxy or ethoxy.

Preferred compounds of formula I are those wherein $R_1$ is hydrogen, halogen or methyl and $R_2$ is halogen, methyl or trifluoromethyl; and also those wherein A is the

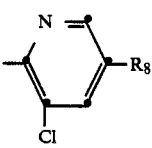

radical, in which $R_8$ is chlorine, trifluoromethyl or perhalogenated ethyl, or in which A is the

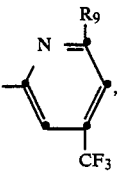

radical, in which $R_9$ is hydrogen or chlorine.

On account of their biological activity, particularly interesting compounds of formula I are those wherein $R_8$ is trifluoromethyl or a member selected from the group consisting of —$CH_2CF_2Cl$, —$CF_2$—$CFCl_2$, —$CCl_2$—$CCl_3$, —$CF_2$—$CCl_3$ or —$CF_2$—$CF_3$; those wherein $R_9$ is chlorine; those wherein the —O—A group is in the 4-position on the phenyl ring; and those wherein the —O—A group is in the 5-position on the phenyl ring.

Particularly preferred compounds of the formula I are those wherein
$R_1$ is hydrogen, fluorine, chlorine or methyl,
$R_2$ is fluorine, chlorine or trifluoromethyl,
$R_3$ is methyl, ethyl, n-propyl, isopropyl, —$CH_2CF_3$ or —$CH_2CCl_3$,
$R_4$ is hydrogen, fluorine, chlorine, bromine or methyl,
$R_5$ is hydrogen, fluorine or chlorine, and
$R_6$ and $R_7$ are hydrogen;
or those wherein
$R_1$ is hydrogen, fluorine or chlorine,
$R_2$ is fluorine,
$R_3$ is methyl, ethyl or n-propyl, and
$R_4$ and $R_5$ are each independently of the other hydrogen, fluorine or chlorine;
or those wherein
$R_3$ is methyl or ethyl, and
$R_4$ and $R_5$ are each independently of the other hydrogen or chlorine.

Further interesting compounds of formula I are those wherein $R_1$ is hydrogen or bromine and $R_2$ is bromine; those wherein $R_4$ is hydrogen or methyl and $R_5$ is methyl; or those wherein $R_3$ is $C_1$-$C_3$haloalkyl containing 1 to 3 halogen atoms, allyl or propergyl.

The term "alkyl" will be understood as meaning straight chain and branched alkyl radicals and, depending on the indicated number of carbon atoms, are for example the following groups: methyl, ethyl, propyl, butyl and pentyl, and the isomers thereof, e.g. isopropyl, isobutyl, tert-butyl, isopentyl etc.

The compounds of formula I can exist in two different geometrically isomeric forms, depending on the spatial disposition of the substituent groups about the

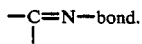

In accordance with conventional chemical nomenclature, these two isomers are designated as the E form and the Z form. The two isomeric forms of the compounds of formula I are shown below as follows:

Z form:

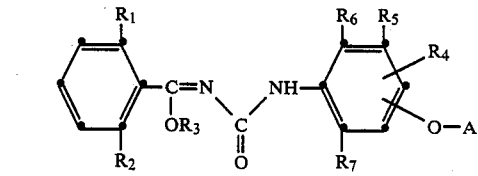

E form:

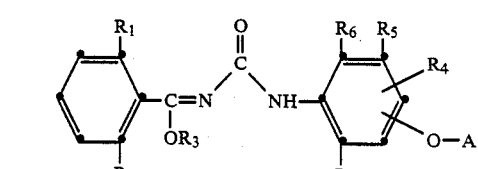

Depending on their spatial structure, the compounds of formula I can exist as pure Z form, pure E form, or as a mixture of both forms.

The compounds of formula I can be prepared by methods analogous to known ones (q.v. U.S. Pat. No. 4,357,347 and European patent specification No. 0.005.944). Thus, for example, a compound of formula I can be obtained by (a) reacting a compound of formula II

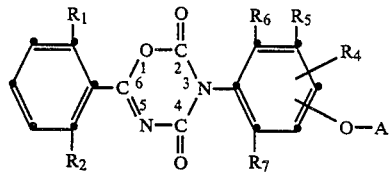

with a compound of formula III

 (III)

or (b) reacting a compound of formula IV

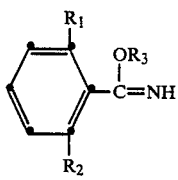 (IV)

with a compound of formula V

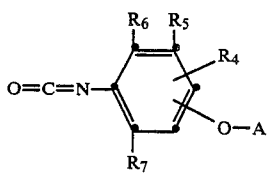 (V)

or with phosgene and a compound of formula VI

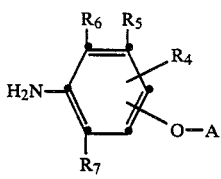 (VI)

in which formulae II to VI above the symbols $R_1$ to $R_7$ and A are as defined above for formula I.

Process (a) above is generally carried out under normal pressure and preferably by direct reaction of the reactants in the temperature range from 20° to 120° C., preferably from 30° to 90° C. The reaction can also be conducted in the presence of an inert solvent. An excess of the alcohol of formula III is conveniently employed as solvent. Proces (b) is normally conducted under normal pressure, in the presence of a suitable inert solvent, and in the temperature range from 0° to 110° C., preferably from 20° to 70° C. If desired, a catalytic amount of a tertiary organic base such as triethylamine may be added to the reaction mixture. Process (b) may also be varied by phosgenating the phenylcarboximidate of formula IV in the temperature range from −20° to +60° C., and subsequently reacting the resultant chlorocarbonylphenylcarboximidate of formula VII

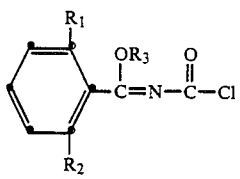 (VII)

with an appropriately substituted pyridyloxyaniline of formula VI in the presence of an acid acceptor, e.g. an inorganic base such as triethylamine, pyridine, choline or the like. Suitable solvents for the above reactions are for example: ethers and ethereal compounds such as diethyl ether, dipropyl ether, dibutyl ether, dioxan, dimethoxyethane and tetrahydrofuran; N,N-dialkylated carboxylic acid amides; esters such as ethyl acetate; aliphatic, aromatic and halogenated hydrocarbons, in particular benzene, toluene, xylene, chloroform, methylene chloride, carbon tetrachloride and chlorobenzene; nitriles such as acetonitrile or propionitrile; and ketones, for example methyl ethyl ketone, methyl isopropyl ketone and methyl isobutyl ketone.

The starting materials of the formulae II to VI employed for the processes of the invention are known or they can be obtained by procedures analogous to known ones. Thus the 3,6diphenyl-1,3,5-oxadiazine-2,4-dione derivatives of formula II can be obtained (q.v. DE-OS Nos. 2732115 and 2905687) by reacting a pyridyloxyphenyl isocyanate of formula V with a benzoyl isocyanate of the formula VII a

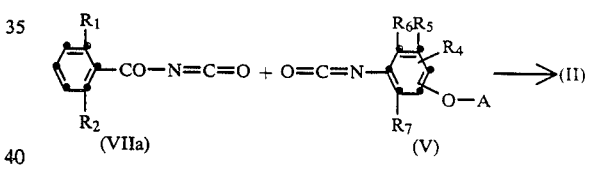

or with a halocarbonylbenzamide of the formula VIII

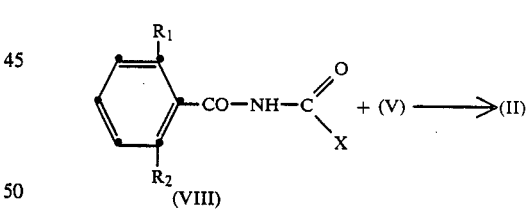

The above-mentioned isocyanates of the formula V can be obtained from the appropriately substituted pyridyloxyanilines of formula VI by conventional phosgenation. The pyridyloxyanilines of formula VI can be obtained for example by reacting a reactive pyridine of formula IX below with an appropriately substituted aminophenol, in the presence of a base (q.v. European patent application No. 0 077 759 and DE-OS Nos. 3 240 975 and 3 241 138). The anilines of formula VI can also be obtained by reacting appropriately substituted nitrophenols of formula X with a pyridine of formula IX and subsequently reducing the nitro group in the resultant compound of formula XI by a conventional procedure [q.v. for example Rec. 21, 271 (1902); J. Am. Soc. 68, 1604 (1964); J. Org. Chem. 11, 378 (1946); Rec. 79, 994 (1970)]:

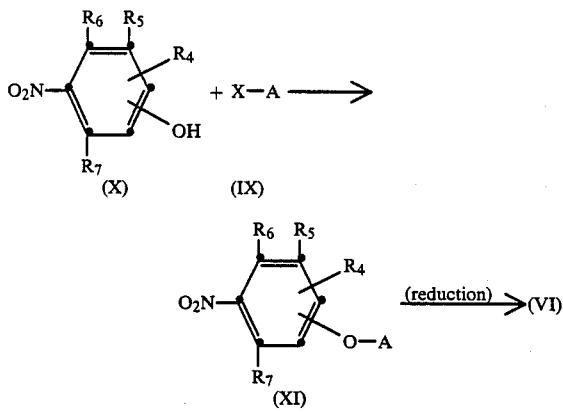

In formulae VII to XI above, $R_1$ to $R_7$ and A are as defined for formula I and X is halogen, preferably chlorine. Phenylcarboximidates of formula IV can be obtained by conventional esterification of corresponding benzamides in a manner known per se (q.v. for example U.S. Pat. No. 4,357,347).

Variously substituted esters of N[[[phenoxyphenyl]amino]carbonyl]phenylcarboximidic acid having insecticidal properties are known from U.S. Pat. No. 4,357,347 and European patent specification No. 0005944. Surprisingly, it has now been found that, compared with these known compounds, the compounds of formula I which contain a pyridyloxyphenyl grouping as essential structural element, exhibit excellent insecticidal activity as pesticides, in particular as insecticides. The substituted N-[[[pyridyloxyphenyl]amino]carbonyl]phenylcarboximidates of the present invention are particularly useful insecticides for plant protection. A particular advantage of the compounds of formula I is their very low mammalian toxicity and that they are also well tolerated by plants.

In particular, the compounds of the formula I are suitable for controlling insects of the orders: Lepidoptera, Coleoptera, Homoptera, Heteroptera, Diptera, Thysanoptera, Orthoptera, Anoplura, Siphonaptera, Mallophage, Thysanura, Isoptera, Psocoptera and Hymenoptera, as well as representatives of the order Acarina of the families: Ioxididae, Argisidae, Tetranychidae and Dermanyssidae.

In addition to their action against flies, e.g. *Musca domestica*, and mosquito larvae, the compounds of formula I are also suitable for controlling plant-destructive feeding insects, especially their larval stages, in ornamentals and crops of useful plants, especially in cotton (e.g. against *Spodoptera littoralis* and *Heliothis virescens*) and in fruit and vegetables (e.g. against *Laspeyresia pommonella*, *Leptinotarsa decemlineata* and *Epilachna varivestis*). The compounds of formula I have a pronounced ovicidal and larvicidal action against insects, especially against larvae of noxious feeding insects. If compounds of formula I are ingested with the feed, then a diminished oviposition and/or reduced hatching rate is observed in many insects, especially in Coleoptera, e.g. *Anthonomus grandis*.

The compounds of formula I can also be used for controlling ectoparasites such as *Lucilia sericata*, in domestic animals and productive livestock, e.g. by treating animals, cowsheds, barns, stables etc., and pastures.

The compounds of formula I are also suitable for controlling the following species of mites which attach crops of fruit and vegetables: *Tetranychus urticae*, *Tetranychus cinnabarinus*, *Panonychus ulmi*, *Broybia rubriculus*, *Panonychus citri*, *Eriophyes piri*, *Eriophyes ribis*, *Eriophyes vitis*, *Tarsonemus pallidus*, *Phyllocoptes vitis* and *Phyllocoptruta oleivora*.

The activity of the compounds of the formula I and of the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates, chlorinated hydrocarbons, and Bacillus thuringiensis preparations.

Compounds of formula I are also combined with particular advantage with substances which exert a pesticidally potentiating action. Examples of such compounds comprise: piperonyl butoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioate.

The good insecticidal activity of the proposed compounds of the formula I according to the invention corresponds to a mortality of at least 50-60% of the above insect pests, in particular harmful insects.

The compounds of the formula I are used in unmodified form, or preferably together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application such as spraying, atomising, dusting, scattering or pouring, are chosen in accordance with the intended objectives and the prevailing circumstances.

The formulations, i.e. the compositions or preparations containing the compound (active ingredient) of the formula I or combinations thereof with other insecticides or acaricides, and, where appropriate, a solid or liquid adjuvant, are prepared in known manner, e.g. by homogeneously mixing and/or grinding the active ingredients with extenders, e.g. solvents, solid carriers, and in some cases surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, or of combinations thereof with other insecticides or acaricides, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained, e.g. from coconut oil or tallow oil. Further suitable surfactants are also the fatty acid methyltaurin salts as well as modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate, or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminepolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan and polyoxyethylene sorbitan trioleate are also suitable non-ionic surfactants.

Cationic surfactants are preferably quaternary ammonium salts which contain, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi-(2-chloroethyl)-ethylammonium bromide.

The surfactants customarily employed in the art of formulation are described e.g. in "McCutcheon's Detergents and Emulsifiers Annual", MC Publishing Corp. Ridgewood, N.J., 1979; Dr. Helmut Stache, "Tensid Taschenbuch", Carl Hauser Verlag, Munich/Vienna.

The pesticidal compositions usually contain 0.1 to 99%, preferably 0.1 to 95%, of a compound of the formula I or combination thereof with other insecticides or acaricides, 1 to 99.9% of a solid or liquid adjuvant, and 0 to 25%, preferably 0.1 to 20%, of a surfactant.

Whereas commercial products are preferably formulated as concentrates, the end user will normally employ dilute formulations of substantially lower concentration.

The copositions may also contain further ingredients, such as stabilisers, antifoams, viscosity regulators, binders, tackifiers as well as fertilisers or other active ingredients in order to obtain special effects.

Formulation examples of solid active ingredients of the formula I or combinations thereof with other insecticides or acaricides (throughout, percentages are by weight)

| 1. Wettable powders | (a) | (b) | (c) |
| --- | --- | --- | --- |
| compound of formula I or combination | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 2. Emulsifiable concentrate | |
| --- | --- |
| compound of formula I or combination | 10% |
| octylphenol polyethylene glycol ether (4–5 moles of ethylene oxide) | 3% |
| calcium dodecylbenzenesulfonate | 3% |
| castor oil polygycol ether (36 moles of ethylene oxide) | 4% |
| cyclohexanone | 30% |
| xylene mixture | 50% |

Emulsions of any required concentration can be obtained from this concentrate by dilution with water.

| 3. Dusts | (a) | (b) |
| --- | --- | --- |
| compound of formula I or combination | 5% | 8% |
| talcum | 95% | — |
| kaolin | — | 92% |

Ready for use dusts are obtained by mixing the active ingredient with the carriers, and grinding the mixture in a suitable mill.

| 4. Extruder granulate | |
|---|---|
| compound of formula I or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded and then dried in a stream of air.

| 5. Coated granulate | |
|---|---|
| compound of formula I or combination | 3% |
| polyethylene glycol 200 | 3% |
| kaolin | 94% |

The finely ground active ingredient or combination is uniformly applied, in a mixer, to the kaolin moistened with polyethylene glycol. Non-dusty coated granulates are obtained in this manner.

| 6. Suspension concentrate | |
|---|---|
| compound of formula I or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

EXAMPLE 1

Preparation of methyl 2-chloro-N-[[[3,5-dichloro-4-(3-chloro-5-trifluoromethyl-2-pyridyloxy)phenyl]amino]carbonyl]phenylcarboximidate With exclusion of moisture, 4.0 g of 3-[3,5-dichloro-4-(3-chloro-5-trifluoromethyl-2-pyridyloxy)phenyl]-6-(2-chlorophenyl)-3,4-dihydro-2H-1,3,5-oxadiazine-2,4-dione are stirred in 70 ml of absolute methyl alcohol for 8 hours at 60° C. The resultant solution is concentrated and the residue is chromatographed through silica gel with dichloromethane. The residue obtained from the concentrated eluates is triturated with hexane and filtered with suction, affording the title compound (compound 1) of the formula

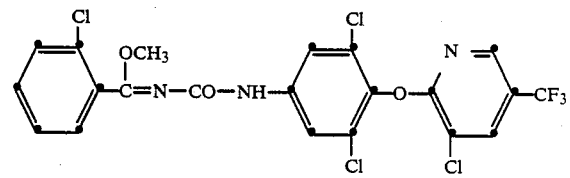

as a white powder with a melting point of 147°–149° C.

The following compounds of formula I are prepared by procedures analogous to that described above:

| Compound | | Physical data |
|---|---|---|
| 2 | | m.p. 134–136° C. |
| 3 | | m.p. 186–187° C. |
| 4 | | m.p. 169–170° C. |

| Compound | | Physical data |
|---|---|---|
| 5 | 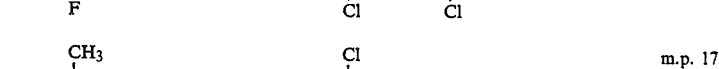 | amorphous product |
| 6 | | m.p. 172–174° C. |
| 7 | | m.p. 155–157° C. |
| 8 | | m.p. 138–141° C. |
| 9 | | m.p. 162–164° C. |
| 10 | | amorphous product |
| 11 | | amorphous product |
| 12 | | m.p. 169–170° C. |
| 13 | | m.p. 162–164° C. |

| Compound | Structure | Physical data |
|---|---|---|
| 14 | 2-Br, OCH₃ / C=N-CO-NH-phenyl(2,6-Cl₂)-O-pyridyl(3-Cl, 5-CF₃) | m.p. 154–156° C. |
| 15 | 2,6-F₂, OC₂H₅ / C=N-CO-NH-phenyl(2,6-Cl₂)-O-pyridyl(3-Cl, 5-CF₃) | m.p. 157–159° C. |
| 16 | 2,6-F₂, OCH₃ / C=N-CO-NH-phenyl(2-CH₃)-O-pyridyl(3-Cl, 5-CF₃) | m.p. 142–144° C. |
| 17 | 2,6-F₂, OCH₃ / C=N-CO-NH-phenyl-O-pyridyl(3-Cl, 5-Cl) | m.p. 173–174° C. |
| 18 | 2-OCH₃, OCH₃ / C=N-CO-NH-phenyl(2,6-Cl₂)-O-pyridyl(3-Cl, 5-CF₃) | m.p. 184–186° C. |
| 19 | 2-OCH₃, OC₂H₅ / C=N-CO-NH-phenyl(2,6-Cl₂)-O-pyridyl(3-Cl, 5-CF₃) | m.p. 151–153° C. |
| 20 | 2-OCH₃, OCH₃ / C=N-CO-NH-phenyl(2-CH₃)-O-pyridyl(3-Cl, 5-CF₃) | m.p. 165–167° C. |

The following compounds of formula I can be prepared in corresponding manner:

| Compound | |
|---|---|
| 21 | 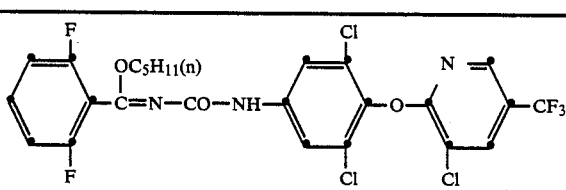 |

-continued
| Compound | |
|---|---|
| 22 | 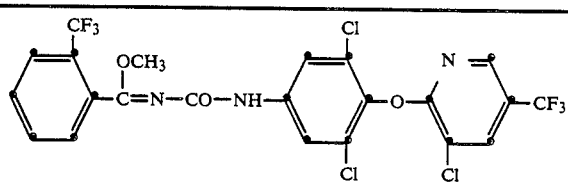 |
| 23 | 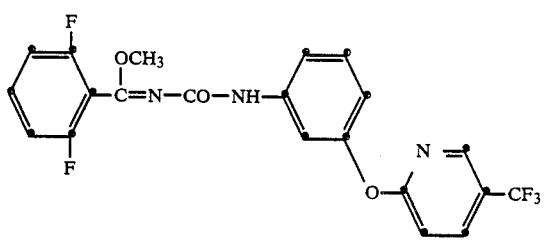 |
| 24 | 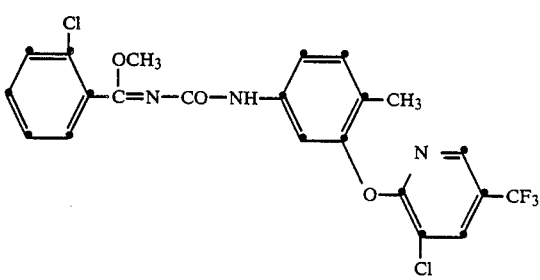 |
| 25 | 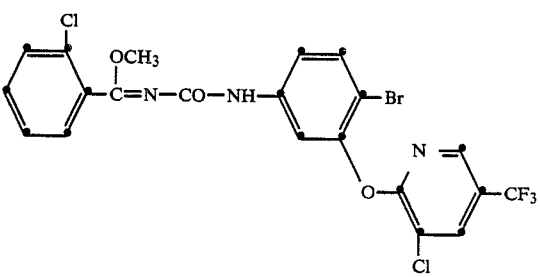 |
| 26 | 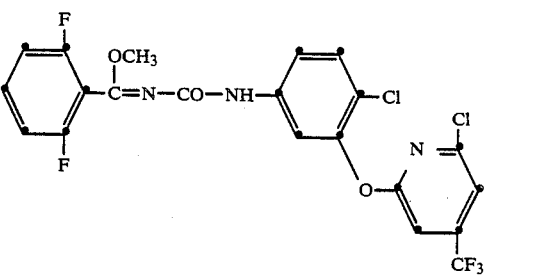 |
| 27 | 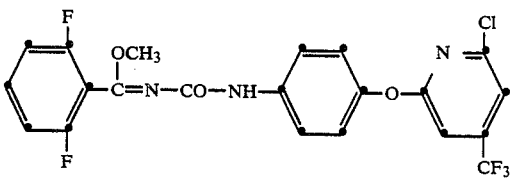 |
| 28 | 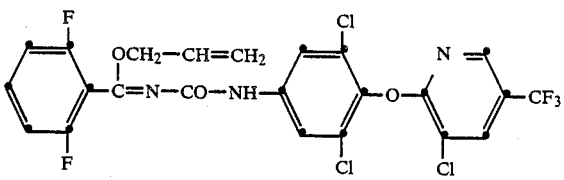 |

| Compound | |
|---|---|
| | -continued |

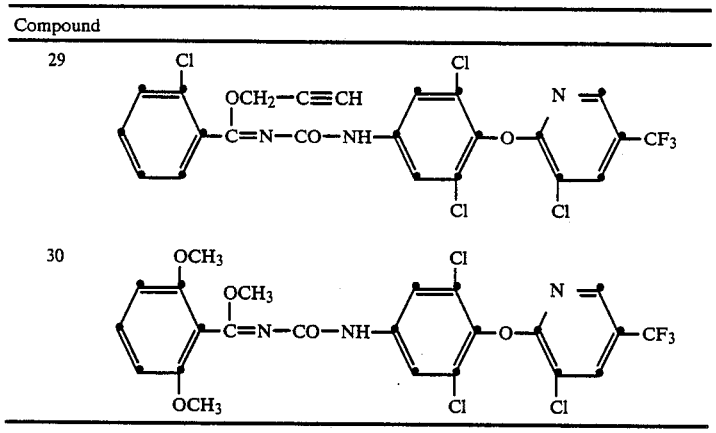

EXAMPLE 2

Action against *Musca domestica*

50 g of freshly prepared nutrient substrate for maggots are charged into each of a number of beakers. A specific amount of a 1% acetonic solution of the respective test compound is pipetted onto the nutrient substrate present in the beakers to give an active ingredient concentration of 400 ppm. The substrate is then thoroughly mixed and the acetone subsequently allowed to evaporate over a period of at least 20 hours.

Then 25 one-day-old maggots of *Musca domestica* are put into each of the beakers containing the treated nutrient substrate for testing with each active ingredient at one of its given concentrations. After the maggots have pupated, the pupae are separated from the substrate by flushing them out with water and then deposited in containers closed with a perforated top.

Each batch of flushed out pupae is counted to determine the toxic effect of the test compound on the maggot development. A count is then made after 10 days of the number of flies which have hatched out of the pupae.

The compounds of formula I obtained according to Example 1 have good activity in this test.

EXAMPLE 3

Action against *Lucilia sericata*

1 ml of an aqueous solution containing 0.5% of test compound is added at 50° C. to 9 ml of a culture medium. Then about 30 freshly hatched *Lucilia sericata* larvae are added to the culture medium, and the insecticidal action is determined after 48 and 96 hours by evaluating the mortality rate. In this test, compounds of the formula I according to Example 1 exhibit good activity against *Lucilia sericata*.

EXAMPLE 4

Action against *Aedes aegypti*

A concentration of 400 ppm is obtained by pipetting a specific amount of a 0.1% solutioon of the test compound in acetone onto the surface of 150 ml of water in a beaker. After the acetone has evaporated, 30 to 40 two-day-old larvae of *Aedes aegypti* are put into the beaker containing the test compound. Mortality counts are made after 1, 2 and 5 days.

In this test, compounds of Example 1 exhibit good activity against *Aedes aegypti*.

EXAMPLE 5

Insecticidal Action against Feeding Insects

Cotton plants about 25 cm high, in pots, are sprayed with aqueous emulsions which contain the test compound in concentrations of 400, 200, 50, 12.5 and 3.0 ppm. After the spray coating has dried, the cotton plants are populated with *Spodoptera littoralis* and *Heliothis virescens* larvae in the $L_3$-stage. The test is carried out at 24° C. and 60% relative humidity. The percentage mortality of the test insects is determined after 120 hours.

EXAMPLE 6

Action against *Epilchna varivestis*

*Phaseolus vulgaris* plants (dwarf beans) about 15–20 cm in height are sprayed with aqueous emulsion formulations of the test compound in concentrations of 800 ppm. After the spray coating has dried, each plant is populated with 5 larvae of *Epilachna varivestis* (Mexican bean beetle) in the $L_4$-stage. A plastic cylinder is slipped over the treated plants and covered with a copper gauze top. The test is carried out at 28° C. and 60% relative humidity. The percentage mortality is determined after 2 and 3 days. Evaluation of feeding damage (anti-feeding effect), and of inhibition of development and shedding, is made by observing the test insects for a further 3 days.

The compounds of Example 1 exhibit good activity in this test.

EXAMPLE 7

Ovicidal Action against *Heliothis virescens*

Corresponding amounts of a wettable powder formulation containing 25% by weight of the test compound are mixed with sufficient water to produce an aqueous emulsion with an active ingredient concentration of 400 ppm. One day-old egg deposits of Heliothis on cellophane are immersed in these emulsions for 3 minutes and then collected by suction on round filters. The treated deposits are placed in petri dishes and kept in the dark. The hatching rate in comparison with untreated controls is determined after 6 to 8 days.

In this test the compounds of Example 1 exhibit good ovicidal action.

EXAMPLE 8

Action against *Laspeyresia pomonella* (eggs)

Egg deposits of *Laspeyrasia pomonella* not more than 24 hours old are immersed on filter paper for 1 minute in an acetonic solution containing 800 ppm of the test compound.

After the solution has dried, the eggs are placed in petri dishes and kept at a temperature of 28° C. The percentage of larvae hatched from the treated eggs and the percentage mortality is evaluated after 6 days. The compounds of formula I according to Example 1 exhibit good activity in this test.

EXAMPLE 9

Influence on the Reproduction of *Anthonomous grandis*

*Anthonomous grandis* adults which are not more than 24 hours old after hatching are transferred in groups of 25 to barred cages. The cages are then immersed for 5 to 10 seconds in an acetonic solution containing 1.0% by weight of the test compond. After the beetles have dried, they are placed in covered dishes containing feed and left for copulation and oviposition. Egg deposits are flushed out with running water twice to three times weekly, counted, disinfected by putting them for 2 to 3 hours into an aqueous disinfectant, and then placed in dishes containing a suitable larval feed. A count is made after 7 days to determine whether larvae have developed from the eggs.

The duration of the reproduction inhibiting effect of the test compounds is determined by monitoring the egg deposits over a period of about 4 weeks. Evaluation is made by assessing the reduction in the number of deposited eggs and hatched larvae in comparison with untreated controls.

The compounds of the formula I according to Example 1 exhibit a good reproduction inhibiting effect in this test.

EXAMPLE 10

Acaricidal Action 12 hours before the test for acaricidal action, *Phaseolus vulgaris* plants are settled by means of an infested piece of leaf from a mass culture of *Tetranychus urticae*. The treated plants infested with the mobile stages which have migrated to the plants are sprayed from a chromatography atomiser with emulsified test solutions each having an active ingredient concentration of 800 ppm so that the plants do not drip. A count of living and dead adults and larvae is made under a stereoscopic microscope after 2 days and again after 7 days. The result is expressed in percent. During the test run, the plants stand in greenhouse compartments at 25° C.

Compounds of the formula I according to Example 1 exhibit good activity in the above test.

EXAMPLE 11

Action Against *Anthonomus grandis* (adults)

Two cotton plants in the 6-leaf stage, in pots, are each sprayed with a wettable aqueous emulsion formulation containing the test compound in a concentration of 100, 50 and 12.5 ppm. After the spray coating has dried (about 1½ hours), each plant is populated with 10 adult beetles (*Anthonomus grandis*). Plastic cylinders, covered at the top with gauze, are then slipped over the treated plants populated with the test insects to prevent the beetles from migrating from the plants. The treated plants are then kept at 25° C. and about 60% relative humidity. Evaluation is made after 2, 3, 4 and 5 days to determine the percentage mortality of the beetles (percentage in dorsal position) as well as the anti-feeding action as compared with untreated controls.

Results of the Biological Tests

The results of biological tests carried out with the compounds of the invention in accordance with the foregoing Examples are reported in the following table. Evaluation of the tests in terms of percentage mortality is made using the following rating:

A: 80–100% mortality at a concentration of 3.0 ppm of the tested compound

B. 80–100% mortality at a concentration of 12.5 ppm of the tested compound

C: 80–100% mortality at a concentration of 50 ppm of the tested compound

D: 80–100% mortality at a concentration of 100 ppm of the tested compound

E: 80–100% mortality at a concentration of 200 ppm of the tested compound

F: 80–100% mortality at a concentration of 400 ppm of the tested compound

—: not tested.

| Compound | Pesticidal activity | | |
|---|---|---|---|
| | *Spodoptera larvae* (Example 5) | *Heliothis larvae* (Example 5) | Anthonomus (Example 11) |
| 1 | B | C | B |
| 2 | B | F | C |
| 3 | D | F | B |
| 4 | E | F | — |
| 5 | C | E | D |
| 6 | F | — | — |
| 7 | B | F | C |
| 8 | C | D | C |
| 9 | E | — | C |
| 10 | C | D | — |
| 11 | E | — | — |
| 13 | C | D | — |
| 14 | A | E | — |
| 15 | D | — | — |
| 16 | B | C | B |
| 17 | F | — | — |

What is claimed is:

1. A compound of the formula I

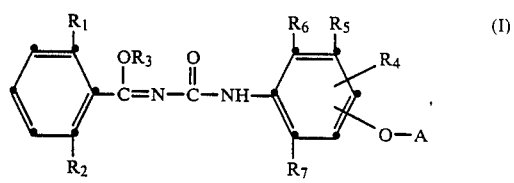

wherein
$R_1$ is hydrogen, halogen or methyl,
$R_2$ is halogen, methyl or trifluoromethyl,
$R_3$ is $C_1$–$C_5$alkyl, $C_1$–$C_3$haloalkyl containing 1 to 3 halogen atoms,
$R_4$ is hydrogen or methyl,
$R_5$ is methyl,
$R_6$ and $R_7$ are hydrogen, and
A is the

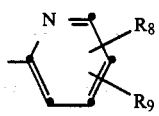

radical, in which R$_8$ is hydrogen, chlorine, trifluoromethyl or perhalogenated ethyl, and R$_9$ is hydrogen, halogen, methoxy or ethoxy.

2. A compound of the formula I according to claim 1, wherein A is the

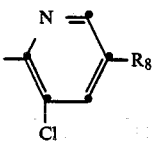

radical, wherein R$_8$ is chlorine, trifluoromethyl or perhalogenated ethyl.

3. A compound of the formula I according to claim 1, wherein A is the

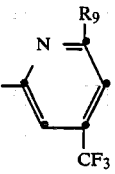

radical, wherein R$_9$ is hydrogen or chlorine.

4. A compound of the formula I according to claim 2, wherein R$_8$ is trifluoromethyl or a member selected from the group consisting of —CF$_2$CF$_2$Cl, —CF$_2$—CFCl$_2$, —CCl$_2$—CCl$_3$, —CF$_2$—CCl$_3$ or —CF$_2$—CF$_3$.

5. A compound of the formula I according to claim 3, wherein R$_9$ is chlorine.

6. A compound of the formula I according to claim 1, wherein the —O—A group is in the 4-position on the phenyl ring.

7. A compound of the formula I according to claim 1, wherein the —O—A group is in the 5-position on the phenyl ring.

8. A compound of the formula I according to claim 1, wherein

R$_1$ is hydrogen, fluorine, chlorine or methyl,
R$_2$ is fluorine, chlorine or trifluoromethyl,
R$_3$ is methyl, ethyl, n-propyl, isopropyl, —CH$_2$CF$_3$ or —CH$_2$CCl$_3$,
R$_4$ is hydrogen, fluorine, chlorine, bromine or methyl,
R$_5$ is hydrogen, fluorine or chlorine, and
R$_6$ and R$_7$ are hydrogen.

9. A compound of the formula I according to claim 1, wherein R$_3$ is C$_1$-C$_3$haloalkyl containing 1 to 3 halogen atoms.

10. A method of controlling pests selected from insects and representatives of the order Acarina, which comprises contacting said pests, their various development stages or the locus thereof, with a pesticidally effective amount of a compound of the formula I

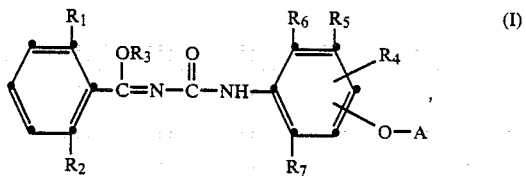

wherein
R$_1$ is hydrogen, halogen, methyl or methoxy,
R$_2$ is halogen, methyl trifluoromethyl or methoxy,
R$_3$ is C$_1$-C$_5$alkyl, C$_1$-C$_3$haloalkyl containing 1 to 3 halogen atoms,
R$_4$ is hydrogen or methyl,
R$_5$ is methyl,
R$_6$ and R$_7$ are hydrogen, and
A is the

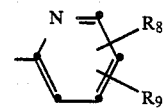

radical, in which R$_8$ is hydrogen, chlorine, trifluoromethyl or perhalogenated ethyl, and R$_9$ is hydrogen, halogen, methoxy or ethoxy, or of the formula II

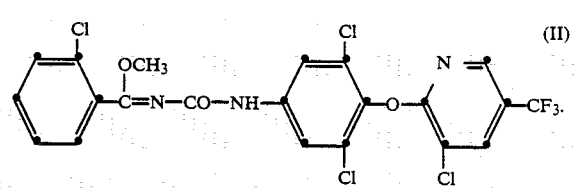

11. A method according to claim 10 for controlling plant-destructive insects.

12. A method according to claim 11 for controlling larval insect stages.

13. A method of claim 10 wherein the compound of formula I is

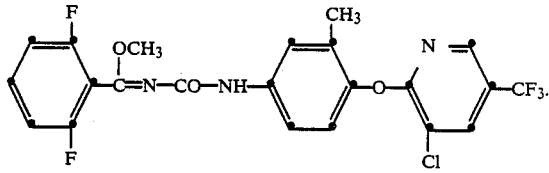

14. A composition of controlling pests selected from insects and representatives of the order Acarina which comprises a pesticidally effective amount of a compound of the formula I

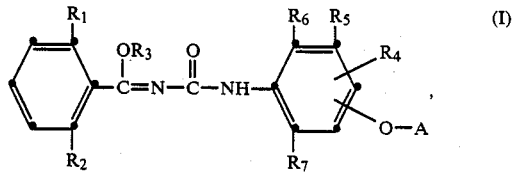

wherein
R$_1$ is hydrogen, halogen, methyl or methoxy,
R$_2$ is halogen, methyl, trifluoromethyl or methoxy, $R_3$ is $C_1$-$C_5$alkyl, $C_1$-$C_3$haloalkyl containing 1 to 3 halogen atoms, $R_4$ is hydrogen or methyl, $R_5$ is methyl, $R_6$ and $R_7$ are hydrogen, and A is the

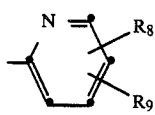

radical, in which $R_8$ is hydrogen, chlorine, trifluoromethyl or perhalogenated ethyl, and $R_9$ is hydrogen, halogen, methoxy or ethoxy or of the formula II

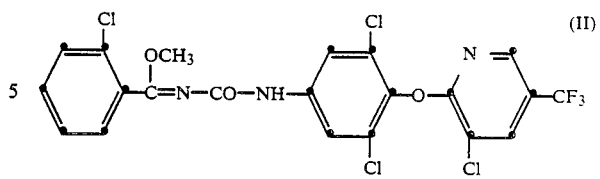

in combination with a pesticidally acceptable carrier or adjuvant.

15. A composition of claim 14 wherein the compound of formula I is

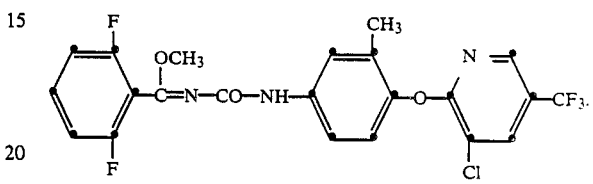

* * * * *